(12) United States Patent
Yunovich et al.

(10) Patent No.: US 6,744,265 B2
(45) Date of Patent: Jun. 1, 2004

(54) AUTOMATED CATHODIC PROTECTION MONITOR AND CONTROL SYSTEM

(75) Inventors: Mark Yunovich, Columbus, OH (US); Neil G. Thompson, Dublin, OH (US)

(73) Assignee: CC Technologies Systems, Inc., Dublin, OH (US)

(*) Notice: Subject to any disclaimer, the term of this patent is extended or adjusted under 35 U.S.C. 154(b) by 74 days.

(21) Appl. No.: 10/115,796

(22) Filed: Apr. 4, 2002

(65) Prior Publication Data

US 2003/0189435 A1 Oct. 9, 2003

(51) Int. Cl.[7] .............................................. G01R 27/08
(52) U.S. Cl. .................. 324/700; 713/450; 204/196.06; 205/724
(58) Field of Search .................. 324/425, 446, 324/444, 448, 449, 450, 691, 693, 700, 713, 714, 715; 204/196.06, 196.01, 196.37, 196.07, 196.1, 196.21, 196.36; 205/724, 726, 727, 730, 734, 735, 736, 740; 73/86; 340/854.5

(56) References Cited

U.S. PATENT DOCUMENTS

| | | | | |
|---|---|---|---|---|
| 5,216,370 A | * | 6/1993 | Bushman et al. | 324/425 |
| 5,587,707 A | * | 12/1996 | Dickie et al. | 340/870.09 |
| 5,814,982 A | | 9/1998 | Thompson et al. | 324/711 |
| 6,107,811 A | | 8/2000 | Caudill et al. | 324/713 |

* cited by examiner

Primary Examiner—N. Le
Assistant Examiner—Vincent Q. Nguyen
(74) Attorney, Agent, or Firm—Frank H. Foster; Kremblas, Foster, Phillips & Pollick

(57) ABSTRACT

An automated, remote control/monitoring system for a cathodic protection system for a buried metallic object based on monitoring multiple coupon test stations, buried next to the metal object, by a central processor, which can individually control multiple cathodic protection rectifiers. Preferably, the reference for potential measurements is a buried coupon having a metallurgy substantially the same as the metallurgy of the buried object.

26 Claims, 7 Drawing Sheets

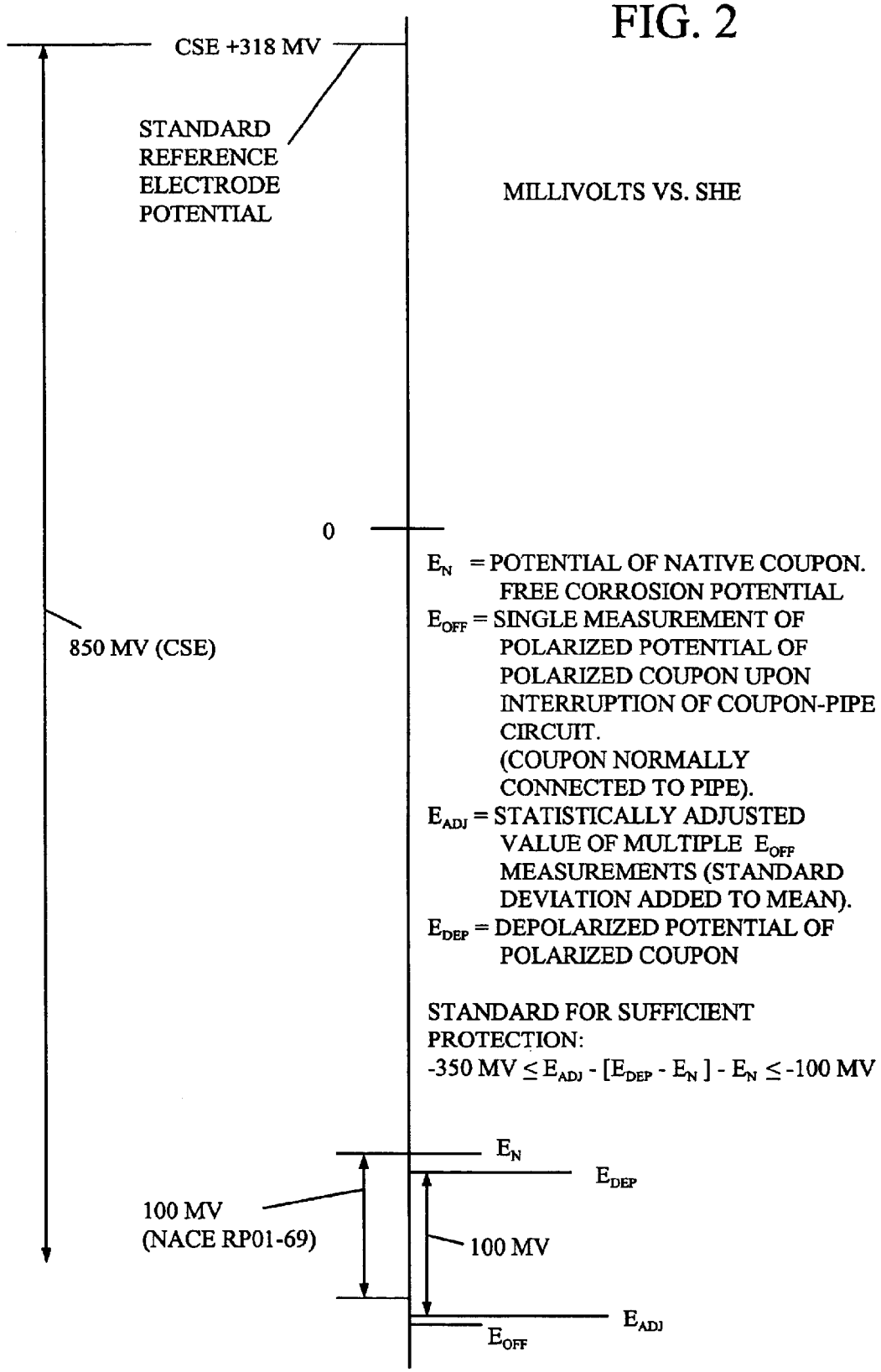

FIG. 3 STATE P1
NO PROTECTION
FAIL
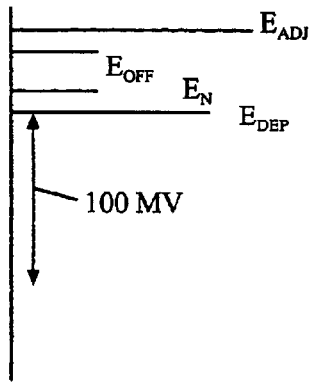
FIG. 4 STATE P2
MINIMALLY PROTECTED
FAIL
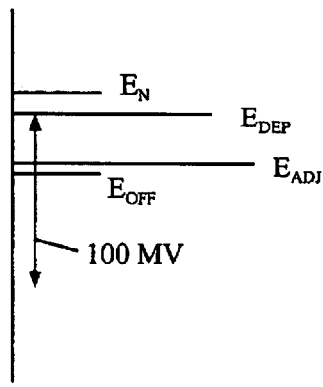
FIG. 5 STATE P3
INSUFFICIENTLY PROTECTED
FAIL
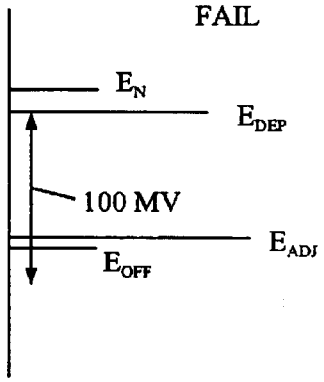
FIG. 6 STATE P4
ADEQUATELY PROTECTED
PASS
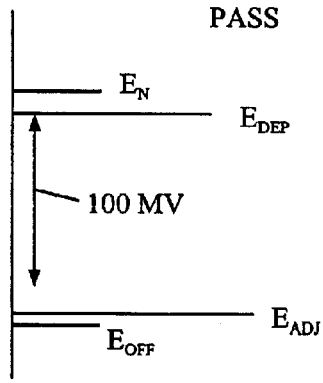
FIG. 7 STATE P5
OVERPROTECTED
EXCEED
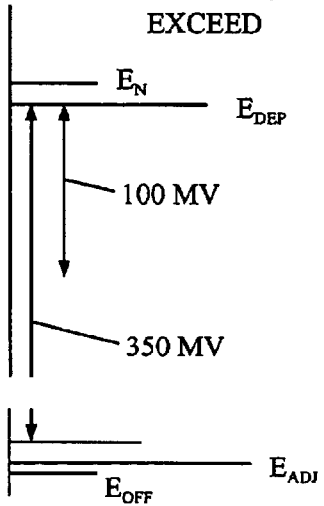
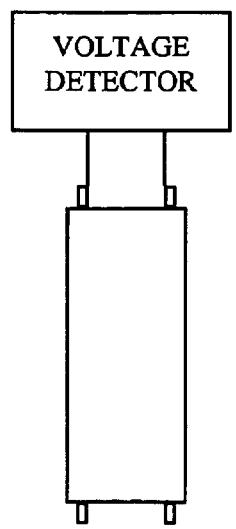
FIG. 12

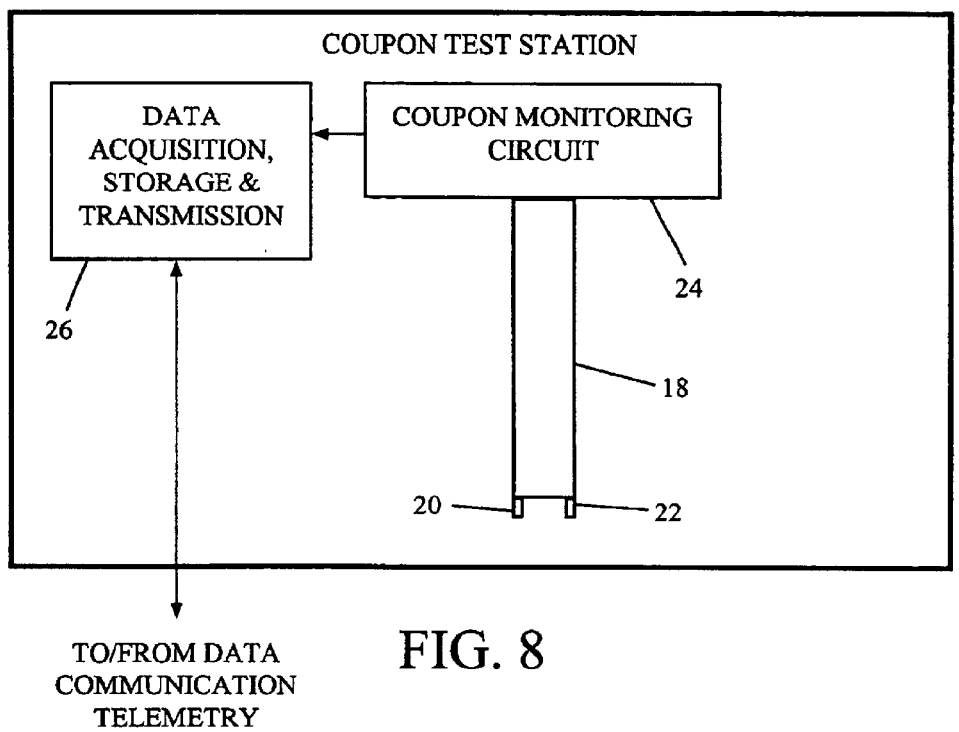
FIG. 8
FIG. 9
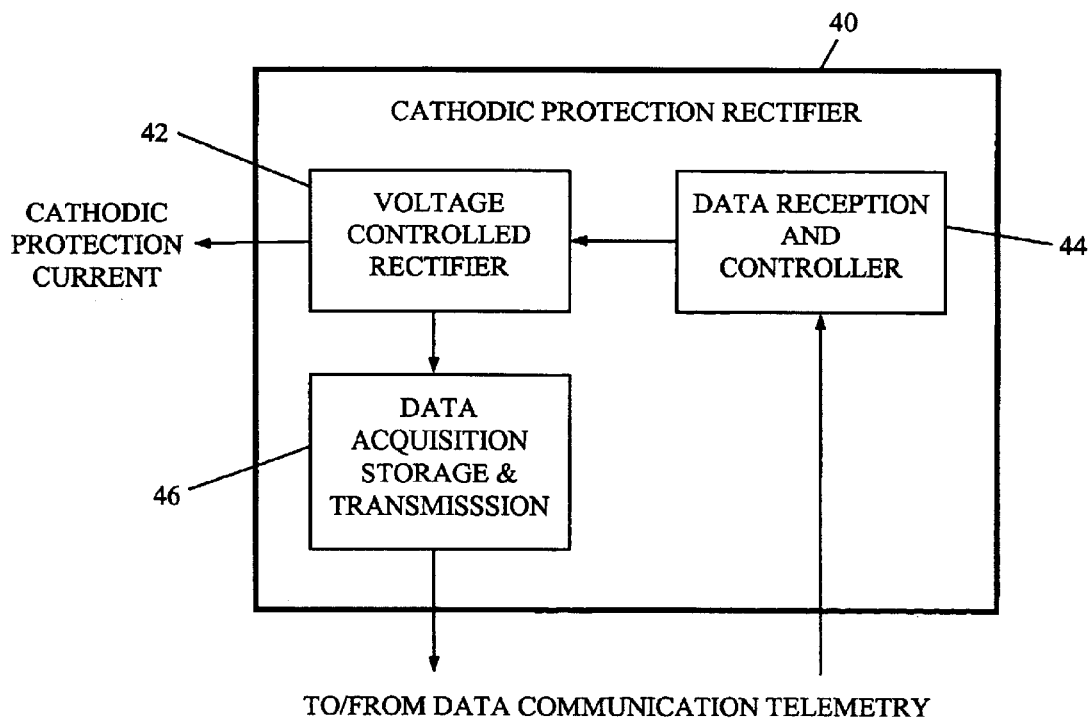

FIG. 11

| PRIORITY STATE | SYMBOL | DESCRIPTION | CRITERIA | RECTIFIER ADJUSTMENT |
|---|---|---|---|---|
| P1 | FAIL "−" | NO PROTECTION | $0\ MV \leq E_{ADJ} - [E_{DEP} - E_N] - E_N$ OR STATISTICALLY ADJUSTED VALUE OF MULTIPLE $I_{ON}$ MEASUREMENTS (STANDARD DEVIATION ADDED TO MEAN) IS POSITIVE. | PROTECTION VOLTAGE OF RECTIFIERS FOR WHICH CTS IS DESIGNATED "LOCAL" INCREASED BY 20%, "CENTRAL" INCREASED BY 10% |
| P2 | FAIL "−" | MINIMALLY PROTECTED | $-50\ MV \leq E_{ADJ} - [E_{DEP} - E_N] - E_N \leq 0\ MV$ | PROTECTION VOLTAGE OF RECTIFIERS FOR WHICH CTS IS DESIGNATED "LOCAL" INCREASED BY 10%, "CENTRAL" INCREASED BY 5% |
| P3 | FAIL "−" | INSUFFICIENTLY PROTECTED | $-100\ MV \leq E_{ADJ} - [E_{DEP} - E_N] - E_N \leq -50\ MV$ | PROTECTION VOLTAGE OF RECTIFIERS FOR WHICH CTS IS DESIGNATED "LOCAL" INCREASED BY 5%, "CENTRAL" INCREASED BY 2.5% |
| P4 | PASS "0" | ADEQUATELY PROTECTED | $-350\ MV \leq E_{ADJ} - [E_{DEP} - E_N] - E_N \leq -100\ MV$ | NO ADJUSTMENT |
| P5 | EXCEED "+" | OVER PROTECTED | $E_{ADJ} - [E_{DEP} - E_N] - E_N \leq -350\ MV$ | PROTECTION VOLTAGE OF RECTIFIERS FOR WHICH CTS IS DESIGNATED "LOCAL" DECREASED BY 5%, "CENTRAL" DECREASED BY 2.5% |

AUTOMATED CATHODIC PROTECTION MONITOR AND CONTROL SYSTEM

CROSS-REFERENCES TO RELATED APPLICATIONS (Not Applicable)

STATEMENT REGARDING FEDERALLY-SPONSORED RESEARCH AND DEVELOPMENT (Not Applicable)

REFERENCE TO APPENDIX

The disclosure of this patent application includes an Appendix which is a copy of a paper to be published shortly after this application is filed.

BACKGROUND OF THE INVENTION

1. Field of the Invention

This invention relates generally to cathodic protection systems for corrosion protection of metal objects which are buried in soil. More particularly, the invention relates to an apparatus and method for continuously monitoring the adequacy of cathodic protection being applied at each of a multiplicity of monitoring stations installed next to and spaced along buried objects, such as pipelines and underground pipe-type electrical power transmission cables, and for automatically controlling, or providing data for manual control of, each individual one of a multiplicity of rectifiers spaced along the same buried object based upon data gathered from multiple neighboring monitoring stations.

2. Description of the Related Art

Buried metal structures, such as pipes, pipe-type cables and storage tanks, are subjected to natural, electrochemical corrosion processes in their underground environment. Although non-conductive coatings are typically applied to such buried objects, the coatings develop flaws or pinholes, known as holidays, that allow the metal object to be directly exposed to the soil electrolyte. This exposure to the soil electrolyte not only permits local corrosion at each holiday, but additionally permits stray electrical currents from other buried objects and above ground sources to be conducted through the soil electrolyte to the buried object and thereby cause further electrochemical corrosion.

Cathodic protection systems have long been applied to buried objects to counteract or at least mitigate the electrochemical corrosion process. Impressed current systems utilize one or more rectifiers to apply a voltage through suitable conductors across the buried object and a buried anode. Typically, these cathodic protection rectifiers are located at spaced intervals along the buried object. Sacrificial anode cathodic protection systems are also used and they are typically also spaced along the buried object. They are powered only by the "battery" which is inherently formed by the dissimilar metals of the anode and buried object connected together by a conductor and immersed in the soil electrolyte.

The technology of cathodic protection recognizes the existence of potentials at the interface between a soil electrolyte and a buried metal. A first relevant potential is the free corrosion potential, also referred to as the oxidation potential, which is the potential at a corrosion interface associated with the oxidation-reduction reactions. Over a period of time, the flow of current causes polarization at the interface and the buildup of an opposing potential as a characteristic of the polarization. Consequently, after polarization, the component corrosion potential and polarization exhibit a resultant potential which is the polarized potential. If the current is halted, the polarization is gradually reduced over time, and the resulting potential is referred to as the depolarized potential. As discussed below, the depolarized potential may not be the same value as the initial free corrosion potential.

Various criteria have been suggested and some have been widely adopted as industry standards for defining a degree of cathodic protection which is considered adequate and are based upon these potentials. One standard (NACE) for typical steel buried objects is the existence of a potential on the buried object which is 850 millivolts more negative than the potential of the standard copper/copper sulfate (CSE) reference electrode placed on top of or buried in the soil. Another standard (NACE) is the existence of a polarized potential which is 100 millivolts more negative than the depolarized potential of the buried metal object.

One prior art method for monitoring this potential difference, to determine whether a particular criterion is met involves installing a standard reference electrode at one or more locations along the buried object together with a conductor connected to the buried object. A technician periodically visits the location and measures the voltage between the standard reference electrode and the buried object using a voltmeter. A responsible person then examines the collected data looking for inadequate voltages and variations from earlier data and, when control is inadequate or excessive, adjusts the output(s) of the appropriate rectifier(s).

Underground stray electrical currents may arise from electrical power installations such as underground power distribution lines or electrically powered mass transit systems. Such stray currents introduce additional complexities and difficulties because they are typically not uniformly distributed along the buried object and may occur more intensely at particular localities and because the magnitude and direction of stray ground currents typically vary with time. DC stray currents contribute to corrosion by causing rapid metal loss at buried object locations serving as current discharge points and by introducing an additional IR-drop in the soil which is a source of error in grade level potential measurements.

The most commonly used potential survey method used to ascertain the existence of the stray current problem for a buried object has been the close interval survey where the pipe-to-soil potential is recorded as a function of distance along the buried object of interest. Any potentials which departed significantly from the potentials at other regions or which deviated significantly from prior surveys, could be identified as possible stray current pickup or discharge points. This has been done by having pipeline maintenance personnel travel to the buried object and make the measurements described above. Single location, time-dependent surveys were also performed by the maintenance staff by monitoring the potential at a chosen location as a function of time. Any significant changes in the recorded potentials could indicate possible intermittent pickup or discharge of stray current.

Advances in technology permitted maintenance staff to carry data loggers, which download data into a computer memory, instead of manually recording measurements from voltmeters. Further advances have permitted some remote detection of the relevant voltage at an individual location using a data communication system to avoid travel to the location.

The technology has been further advanced by the introduction of coupons. A coupon is a metal electrode, buried in the soil, and having essentially the same metallurgical composition as the metal of the buried metal object which is being protected. Apparatus and methods for using coupons are illustrated in U.S. Pat. Nos. 5,814,982 and 6,107,811. These two patents are herein incorporated by reference because the subject matter described in those patents may be used and are preferred for use in connection with the subject matter of the invention disclosed herein.

With coupon technology, a bare coupon is buried near the buried metal object with the coupon normally electrically shorted to the buried object through an electrical lead wire so that the coupon is subjected to the same cathodic protection as the buried object. To permit an accurate potential measurement locally from the grade level, a plastic tube is installed around the coupon to minimize the IR drop in the polarized coupon potential measurement. The coupon-pipe circuit can be interrupted thereby interrupting the cathodic protection of the coupon as well as any stray currents to the coupon and permitting an accurate measurement of the coupon-to-soil off-potential without interrupting the protection to the buried pipe itself. The prior art measures this off potential, $E_{OFF}$, using a standard reference electrode. Typically, the off potential is measured a short time interval, such as 100 milliseconds, after the connection to the cathodic protection system is interrupted. This interval permits the system to settle and transients to die out but is short enough so that no significant depolarization of the coupon has occurred.

The prior art has also used a form of feedback control for controlling a cathodic protection rectifier. In such a system, an analog feedback control system monitors a pipe-to-soil potential with the cathodic protection turned off (some did it with the cathodic protection remaining on) and this measurement was used in a conventional feedback control loop to control the voltage applied by a single rectifier associated with the measurement location.

A deficiency in the prior art exists because stray currents affect the buried object differently at different locations along its length as a result of stray currents arising from other discrete buried objects, such as neighboring, cathodically protected pipelines. Therefore, there is often a wide variation in stray current characteristics at different locations along the length of the buried object. In addition to these substantial spatial variations, stray currents are often dynamic in nature because they vary with time on an hourly, daily and seasonal basis. Consequently, there is a need for a cathodic protection monitoring and control system which can respond to both the spatial and the temporal variations in cathodic protection needs. There is, therefore, a need for a system which can gather and utilize voltage measurement and other data inputs from multiple monitoring sites spaced along the buried object and is able to provide both spatial and temporal responsiveness.

Furthermore, there is a need for apparatus and methods which can utilize the inputs from multiple monitoring sites to individually adjust one or more rectifiers in response to data obtained from multiple monitoring sites along the buried object in order to optimize system resources and minimize cost while providing adequate protection to each segment of the buried object.

In the past, potential measurements which were made to determine the adequacy of the cathodic protection have often been made with reference to the standard reference electrode, such as a copper/copper sulfate reference electrode. There is, however, a need for an improved measuring method and for an improved reference electrode for potential measurements which will be more durable, more accurate and will account for variations in soil conditions, such as seasonal changes in soil moisture, to allow measurements which more accurately reflect the actual protection applied to the buried metal object despite changes in soil conditions.

BRIEF SUMMARY OF THE INVENTION

This invention is directed to an automated data collection and monitoring system, and additionally a control system, for a cathodic protection system having a multiplicity of impressed current cathodic protection circuits, such as rectifiers, electrically connected to the buried object. A multiplicity of test stations are also installed at spaced intervals along the object. Each test station has at least one buried reference electrode, a polarized coupon switchable into and out of electrical connection with the object and having a metallurgical composition similar to the object, and a voltage detection circuit in electrical connection to, and for measuring the potential between, the polarized coupon and the reference electrode. A data communication telemetering system for transmitting potentials detected by the voltage detection circuit connects each of the test stations to a remotely located central control-processing unit which acquires data, as detected at each test station, representing at least the potential, $E_{OFF}$, of the polarized coupon when that coupon is disconnected from the buried object and preferably also the potential, $E_{ON}$, of that coupon when it is connected and the current $I_{ON}$ flowing between the polarized coupon and the buried object. Preferably the reference electrode also has a metallurgical composition substantially the same as the object. Preferably the central control processing unit analyzes the data and determines the adequacy, inadequacy and excessiveness of the cathodic protection of the buried object in the vicinity of each test station. The central computer may also be connected through the telemetering system to one or more of the cathodic protection system rectifiers and be programmed with a control algorithm for controllably adjusting the voltage or current of the cathodic protection system which is applied to effect protection. Some of the principles of the invention are also applicable to discrete buried objects, such as a buried storage tank, which utilizes only a single test station and a single cathodic protection circuit.

BRIEF DESCRIPTION OF THE SEVERAL VIEWS OF THE DRAWINGS

FIG. 2 is a graph illustrating the potentials which are referenced and includes definitions of them.

FIGS. 3–7 are segments of potential graphs, similar to FIG. 2, each illustrating a different protection state.

FIG. 8 is a block diagram illustrating the components of a coupon test station constructed in accordance with the present invention.

FIG. 9 is a block diagram illustrating the components of a cathodic protection rectifier constructed in accordance with the present invention.

FIG. 11 is a table illustrating the protection criteria for determining the adequacy, inadequacy or excessiveness of the cathodic protection.

FIG. 12 is a block diagram illustrating a preferred potential measurement apparatus and method utilizing a native coupon as the reference.

Figure 1:
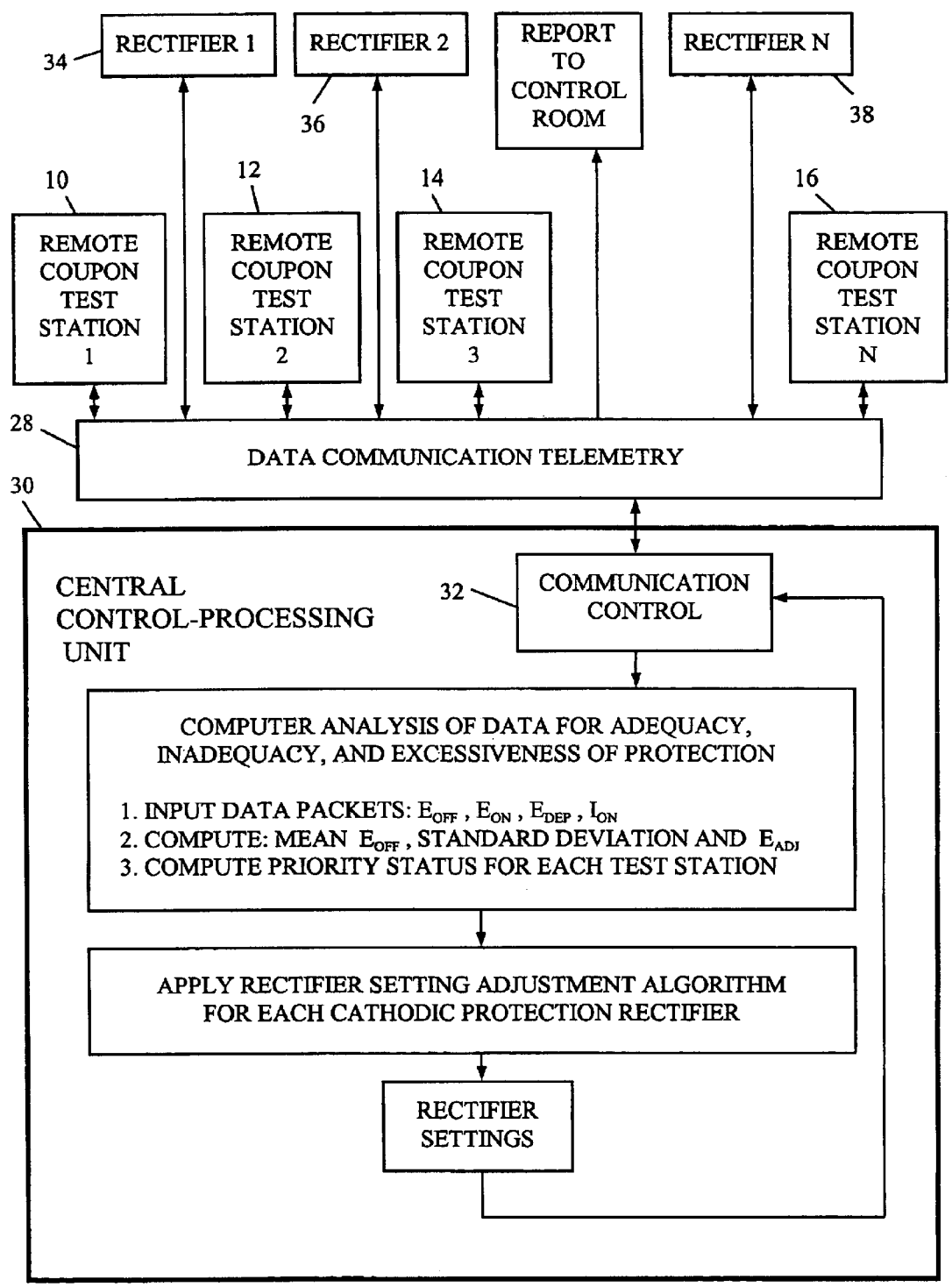
FIG. 1 is a block diagram illustrating the apparatus of the preferred embodiment of the invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other circuit elements where such connection is recognized as being equivalent by those skilled in the art. In addition, many circuits are illustrated which are of a type which perform well known operations on electronic signals. Those skilled in the art will recognize that there are many, and in the future may be additional, alternative circuits which are recognized as equivalent because they provide the same operations on the signals.

DETAILED DESCRIPTION OF THE INVENTION

Structure of the Preferred Apparatus

The apparatus of the preferred embodiment of the invention is illustrated in FIGS. 1, 8, 9, 12, 13, and the two patents, cited above and incorporated by reference, as subsequently described. Referring to FIG. 1, a multiplicity of coupon test stations 10, 12, 14 and 16 are installed at spaced intervals along the buried metal object. They are preferably installed at critical points, particularly the known discharge points for stray current. For example, typically there may be ten test stations along a five to ten mile buried object and this same length may have three rectifiers. The remote coupon test stations preferably are structurally like those shown in U.S. Pat. Nos. 5,814,982 and 6,107,811, although some electrical connections are different as subsequently described.

As described in more detail in U.S. Pat. No. 5,814,982, each test station has a pair of coupons, preferably cylindrical rods, both of which have a metallurgical composition which is substantially the same as the metallurgical composition of the buried metal object being protected. Each test station has at least one buried permanent reference electrode. Although the electrode can be the conventional copper/copper sulfate reference electrode illustrated in U.S. Pat. No. 5,814,982, in the preferred embodiment of this invention, one of those coupons is utilized as a reference electrode. The other coupon is used as a polarized coupon which is switchable into and out of electrical connection with the buried metal object in order to detect a voltage representing the polarized potential of the buried metal object. A standard reference electrode may be included at each test station so that measured potentials also may be referenced to a standard electrode if that measurement is desired.

As illustrated in FIG. 8 and U.S. Pat. No. 5,814,982, each coupon test station has a nonconductive tube 18 surrounding coupons 20 and 22 which extends into the soil as illustrated in the patent. Each coupon test station is also provided with a coupon monitoring and data storage circuit 24 of a type commonly used in data telemetry such as that described in more detail in U.S. Pat. No. 6,107,811. Additionally, each coupon test station is provided with a data communication circuit 26 of the type commonly used in data telemetry and specifically of the type illustrated and described in the same patent and below. The coupon monitoring and data storage circuit 24 includes a voltage detection circuit which is in, or is switchable into, electrical connection to, and for measuring the potential between, the polarized coupon and the reference electrode, which is preferably the other coupon. For example, the polarized coupon may be the coupon 22 and the reference electrode may be the coupon 20. FIG. 12 illustrates the voltage detection circuit connected between the two coupons 20 and 22, one used as the reference and the other used as the polarized coupon. The voltage detector circuit is connected to a data storage 26 (FIG. 8) for storing the value of the detected potential.

Referring again to FIG. 1, the remote coupon test stations are connected to data communication telemetry 28 including the data transmission circuit 26. The data communication telemetry is preferably a commonly used data carrier such as, for example, ordinary telephone lines. The data communication telemetry 28 is connected to a remotely located central control-processing unit 30 for transmission of data to it. In this manner each test station is connected through the data communication telemetry system to the central control-processing unit for transmission of data representing the voltage detected at each test station from each test station to the central control-processing unit.

Although the central control-processing unit 30 may be a special purpose data processing system, it is preferably a general purpose digital computer of common design having stored data and instructions for analyzing the data. However, as described below, the instructions are particularly designed according to an algorithm for determining the adequacy, inadequacy and excessiveness of the cathodic protection of the buried object in the vicinity of each coupon test station.

As known to those skilled in the art, the central control-processing unit 30 has a conventional communication control circuit 32 for receiving and inputting data from the data communication telemetry 28. As will be seen from the following description, the communication control circuit 32 is designed for two-way communication so that data also may be communicated in both directions between the central control-processing unit 30 and each of a multiplicity of cathodic protection circuits, typically rectifiers, 34, 36 and 38 through the data communication telemetry system 28. Typically there are more rectifiers and considerably more coupon test stations than illustrated in FIG. 1, but they are replications of those illustrated.

In order to control the rectifiers 34–38, the central control-processing unit is programmed with stored data and instructions for controllably adjusting an electrical cathodic protection parameter, such as rectifier output voltage or current, individually for each of the cathodic protection circuits 34–38 in response the detection of adequate, inadequate or excess protection. As discussed below, the adjustment of each cathodic protection circuit is preferably based upon data from multiple test stations.

FIG. 9 illustrates a cathodic protection circuit 40 of the present invention. The prior art illustrates a variety of cathodic protection rectifiers, including some which are provided with a voltage controlled rectifier 42. For use with the present invention when the central control-processing unit 30 controls the cathodic protection rectifier, each rectifier is provided with a data reception and control circuit 44 for the input of control data and a data acquisition storage and transmission circuit 46 for holding and communicating data from the rectifier through the data communication telemetry 28 to the central control-processing unit 30. These circuits may be of conventional design. The data transmitted from each rectifier represents a parameter which is indicative of its present state of operation such as its voltage or current being applied to the buried metal object.

Figure 13:
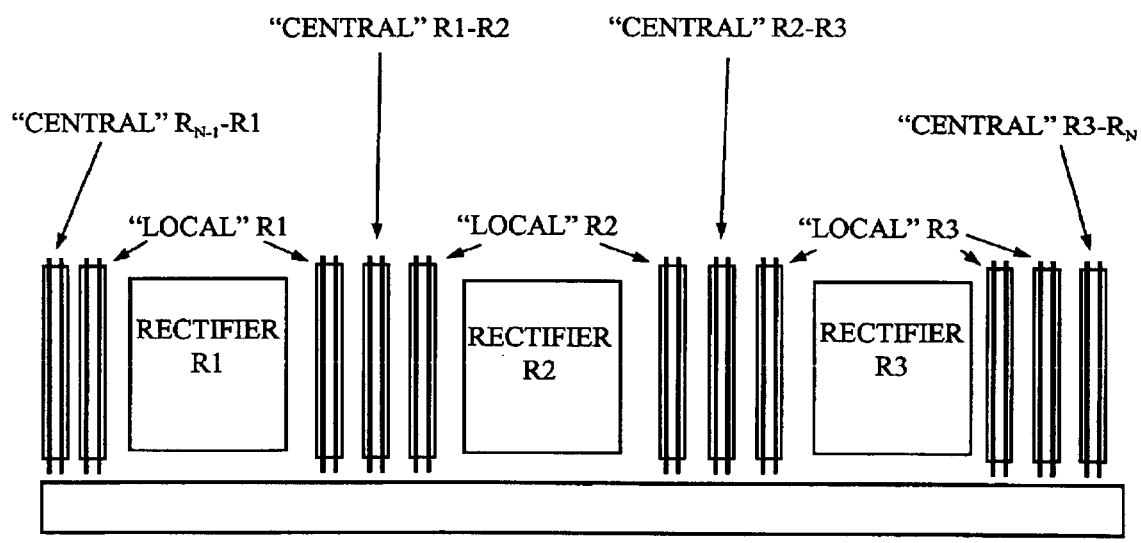
FIG. 13 is a block diagram illustration to positioning of coupon test stations and rectifiers along a buried metal object.

FIG. 13 illustrates a typical arrangement of rectifiers and coupon test stations. Although rectifiers and test stations may be arranged with a one to one correspondence so that each test station is located physically near and is associated with one rectifier, more typically there may be a plurality of test stations at various distances between rectifiers. In order to manage multiple coupon test stations spaced along the buried object more easily and to permit analysis of the data from them so that appropriate control responses may be transmitted back to the rectifiers, the stations are given designations based upon their location relative to the rectifiers. Those coupon test stations which are near a rectifier are designated as "local". Those coupon test stations which are between rectifiers in a location where they are not considerably more closely associated with one rectifier than with other rectifiers, are designated as "central". Multiple test stations near a rectifier may be assigned the same "local" designation and similarly multiple test stations between rectifiers may be assigned the same "central" designation. These designations are assigned on a subjective judgment basis by the engineer who installs and sets up the system.

Although a variety of instrumentation is commercially available to provide data monitoring, acquisition and transmitting capabilities, two off-the-shelf units which were tested with the present invention are a data acquisition and transmission instrument identified as CORD-3 manufactured by Corexco of Dorval, Canada and a unit designated CORD-POT, also manufactured by Corexco, which was interfaced with the rectifier. Although, as described above, land telephone lines were used for digital communication, alternative means of data transmission may also be employed, such as a dedicated cable circuit, wireless transmission either radio or cellular, or utilization of the metallic body of the object for information transfer. Conventional modems and other data transmission circuitry, which are known to those skilled in the art, may also be employed.

Potentials and Reference for Measuring

As known to those skilled in the art, measurements used for evaluating the effectiveness of cathodic protection are based upon making a measurement which is indicative of the polarized potential of the protected, buried metal object. Industry standards require a minimum polarized potential. A polarized potential of less magnitude represents inadequate protection, and a polarized potential which exceeds that value represents a waste of electrical energy and may be associated with damage to the protective coating on the buried object. The measurement of polarized potential requires measurement of a voltage with respect to a reference electrode. The location of the reference electrode relative to the buried object can be a source of measurement errors. Consequently, continuous monitoring for controlling cathodic protection systems requires a permanent, reliable, accurate reference electrode. Although a standard copper/copper sulfate reference electrode could be used for measuring polarized potential at a multiplicity of test stations and for controlling a multiplicity of rectifiers, such electrodes are not sufficiently permanent. Therefore, it is advantageous to utilize a native coupon of a coupon test station as the reference electrode because it will provide accurate data for a longer time with the present invention. A native coupon is a coupon having substantially the same metallurgical composition as the protected buried object. It is buried in the soil with the other test station structures as described in U.S. Pat. Nos. 5,814,982 and 6,107,811 but, unlike what is described in those patents, a coupon is preferably used in the present invention as the reference for making potential measurements. The native reference coupon is not connected to the cathodic protection system at any time and therefore is freely corroding in the soil. Consequently, its potential is the free corrosion potential for its metallurgical composition. More particularly, it is the free corrosion potential in the particular soil environment in which it is placed near the surface of the buried metal object being protected and therefore its potential represents the free corrosion potential of the buried metal object. This permits the 100 millivolt polarization criterion to be directly applied by referencing the off potential, $E_{OFF}$, of the other, polarized coupon to the free corrosion potential of the native coupon.

The 100 millivolt polarization criterion (NACE) requires that the polarized potential of the buried protected object be at least 100 millivolts more negative than its depolarized potential. In an ideal installation, the initial free corrosion potential of the native reference coupon, the depolarized potential of the polarized coupon and the depolarized potential of the buried metal object are all equal to the free corrosion potential for the particular metallurgical composition. However, with the passage of time in the buried environment, the depolarized potential of the polarized coupon like the depolarized potential of the buried metal object may shift due to the build up of a barrier of cathodic-reaction products during application of cathodic protection currents.

This change over time of the depolarized potential of the polarized coupon and the buried metal object which its potential represents is accommodated in the present invention by periodically disconnecting the cathodic protection circuit from the polarized coupon and permitting it to depolarize. After depolarization, its depolarized potential is measured and recorded. One method for recording this depolarized is to have engineering personnel who are servicing the installation manually measure the depolarized potential using the manual measurement techniques of the prior art. The measurement data can then be manually keyed into the central control-processing computer. Alternatively, this measurement can be automated and measured remotely. This is particularly easy to do with the preferred embodiment of the invention because the depolarized potential is measured as the voltage between the same two electrodes between which the off potential and the on potential are measured, namely, the native coupon and the polarized coupon. The only difference is that the depolarized potential is measured between these coupons only after the cathodic protection has been disconnected for a sufficient time to permit depolarization of the polarized coupon. With the automated measurement of the depolarized potential, the value of the depolarized potention or any change in it is stored directly in data memory and used as described below.

The length of time necessary for depolarization varies substantially depending upon the size of the buried object, soil conditions and other variables. However, as an example, every six months, the polarized coupon is disconnected from the cathodic protection system and allowed to depolarize for a stabilization period until its potential becomes constant with time. For example, this stabilization may be for a few hours, a few days or a few weeks. The depolarized potential is then measured and either the depolarized potential or its change is stored in data memory.

A concern with prior uses of polarized coupons is whether the 100 millivolt criterion when measured against a standard reference electrode, e.g. CSE, insured sufficient protection despite seasonal variations that occur, such as variations in soil moisture, over the course of a year. Because the potential measurements in the invention are preferably referenced to a native coupon and that native coupon goes through the same varying moisture conditions as the polarized coupon which is subjected to cathodic protection and as the buried metal object, measurements are more accurate in the varying moisture conditions so that self-regulating updating of the criterion can be accomplished.

Therefore, the present invention allows for continuous adjustment of the cathodic protection criterion to account for both changes in soil conditions as well as variations in the depolarized potential of the polarized, protected coupon which is exposed to the same soil conditions, stray currents and cathodic protection currents as the buried metal object and consequently has a potential which closely represents the polarized potential of the buried metal object. As a result, using the native coupon as a reference not only permits the previously known advantages of a polarized coupon, namely that its potential can be measured without necessitating disconnection of the protected metal object from the cathodic protection system to provide a measurement of the polarized potential of the buried metal object, but also ensures that both the reference coupon and the protected polarized coupon are subjected to the same soil conditions as the buried metal object so that the potentials which are measured remain, under these varying conditions, always representative of the polarized potential of a similarly-sized defect in the external coating of the buried metal object.

FIG. 2 represents the potentials which are used and referred to in connection with practicing the present invention, both those which are familiar to those skilled in the art and those which are unique to the present invention. FIG. 2 shows $E_{OFF}$ which is a single measurement of the polarized potential of the polarized coupon, which is the coupon normally connected to the buried metal object and subjected to cathodic protection. However, when the polarized coupon is disconnected from the buried metal object in the cathodic protection system and its potential is measured, its measured $E_{OFF}$ represents the polarized potential of a similarly-sized defect in the external coating the buried metal object. According to one industry standard, $E_{OFF}$ should be at least 850 millivolts (CSE) less than, that is more negative than, the potential of the standard reference electrode illustrated in FIG. 2.

$E_N$ is the free corrosion potential of the native coupon and therefore represents the free corrosion potential of the similarly-sized defect in the external coating of the buried, protected metal object. $E_{DEP}$ is the depolarized potential of the polarized coupon which, for the reasons described above, may vary and be more or less than the free corrosion potential $E_N$.

Unlike the prior art, the present invention permits the essentially continuous measurement of $E_{OFF}$. For example, a measurement of $E_{OFF}$ may be made every ten seconds. Each measurement is stored in a data buffer. After a series of such measurements, the set of measurements are statistically analyzed to obtain a value to use as an $E_{OFF}$ for the interval over which these samples were taken. For example, 360 measurements of $E_{OFF}$ may be taken at 10 second intervals over one hour. Conventional, statistical analysis, and the conventional computer instructions for making the analysis, are applied to these data points or samples. Preferably, the mean and the standard deviation of these data points is found, and the magnitude of the standard deviation is then added to the mean to obtain a resulting $E_{ADJ}$. The value of $E_{ADJ}$ is a statistically derived value of $E_{OFF}$ for the time interval over which the samples were taken. $E_{ADJ}$ is then used in place of $E_{OFF}$ measurements to determine the adequacy of protection in the vicinity of each test station.

Detection of Other Electrical Parameters

Although the detection of $E_{OFF}$ followed by its statistical analysis as described above is preferred, it is often desirable to detect additional parameters to provide additional information to a user and/or to use in computer analysis and control. These electrical parameters have been identified and measured by those skilled in the art. Additionally, the prior art has developed standards for determining the adequacy of protection for some of them as it has developed the standards for $E_{OFF}$ which are described above. However, the principles of the present invention may be also applied to these other electrical parameters and used to monitor and to determine the adequacy or inadequacy of the cathodic protection, although they are believed to not be as accurate an indication of the state of that protection. Additionally, values of $E_{OFF}$ which have not been statistically adjusted could also be used.

One important parameter is the current $I_{ON}$ flowing through the electrical connection between the buried object and the polarized coupon. This current is the protection current which flows between the buried object and the polarized coupon in the vicinity of the coupon test station. When this current is measured with a zero resistance ammeter or current detection circuit in order to get a more accurate value, it is sometimes referred to as $I_{ZRA}$. This current value is preferably used as described below and, although not preferred, the principle of the present invention may be applied to use this current as a measurement of the adequacy of the cathodic protection.

Another electrical parameter is the voltage, $E_{ON}$, between the reference electrode and the polarized coupon while the electrical connection is maintained between the polarized coupon and the buried object and cathodic protection is being applied. Since this parameter is a potential measured between the same two electrodes which are used to measure $E_{OFF}$, the same voltage detection circuit may be used to measure it. Preferably, this voltage is detected with the present invention so that it may be reported to users who desire to have it. Although not preferred, it too could be used to determine the adequacy of the cathodic protection.

Yet another electrical parameter is the depolarized voltage, $E_{DEP}$, of the polarized coupon. This voltage is, in the most preferred embodiment of the invention, used as described below. It is also a potential which is measured between the reference electrode and the polarized coupon and therefore the same voltage detector can be used to detect it as used to detect the other potentials. However, it is measured after the electrical connection of the polarized coupon to the buried object has been disconnected so that no cathodic protection is applied to the polarized coupon and only after the disconnection has been for a time period which is sufficiently long that the polarized coupon has been permitted to depolarize. This depolarized potential, $E_{DEP}$, of the polarized coupon can also be used with the principles of the present invention to determine the adequacy of the cathodic protection, although that is not preferred.

Protection Adequacy Criteria

The central control-processing unit polls all the coupon test stations through the data communication telemetry multiple times each day at user specified intervals, for example, once every ten or fifteen minutes for metropolitan stations where changes occur more rapidly or every three hours for rural stations. The polling frequency can be changed, for example the frequency can be reduced after multiple repetitions of similar data. The central control-processing unit downloads and logs in data packets from the data acquisition units of the test stations. The packet consists of potential and current data stored by the test stations. Most importantly, this data consist of the series of $E_{OFF}$ measurements forming the data points. It may also include $E_{ON}$ measurements and $I_{ZRA}$ measurements, the latter being defined in U.S. Pat. No. 6,107,811. Each of the $E_{OFF}$ measurements represents the voltage between the native reference coupon and the polarized coupon at the time of measurement.

The primary criterion for effective cathodic protection is based upon a comparison of the potential difference between the potential of the polarized coupon $E_{OFF}$ and the potential of the native reference coupon $E_N$. The initial criterion is that $E_{OFF}$ minus $E_N$ be less than −100 millivolts (i.e. absolute value of difference greater than 100). However, two adjustments from these values are made. The first adjustment is that the multiple data points for the multiple measurements of $E_{OFF}$ are statistically analyzed as described above and the value of $E_{ADJ}$ is used as a composite $E_{OFF}$ for an interval of time. The second adjustment is made in the event that the original open circuit, depolarized potential of the polarized coupon has varied from the free corrosion potential of that coupon as described above. In that event, the depolarized potential $E_{DEP}$ is effectively substituted for $E_N$. Consequently, the basic criterion becomes that $E_{ADJ}$ must be, for adequate protection, at least 100 millivolts more negative than $E_{DEP}$, that is 100 millivolts plus the shift in the depolarized potential from $E_N$ to $E_{DEP}$.

Although it is theoretically possible to thereby detect three states, (1) more than, (2) equal to, or (3) less than −100 millivolts, it is preferred and considerably more practical to define contiguous ranges or intervals of possible measurements with each range being a category of protection state, also referred to as a priority state. Five voltage intervals are preferred to define five categories of protection states. These priority states are illustrated in FIGS. 3–7 and FIG. 11, and each state represents a potential falling within its assigned range. Three categories are defined for under protection conditions and designated as "fail". One category is provided for over protection and designated as "exceed". The final category for adequate protection is designated as "pass". Alternative ranges can be defined and used. The following mathematical steps are performed for each test station to determine a priority state for each test station.

Priority state P1 is illustrated in FIG. 3 for which no protection exists and the state is therefore designated "fail". In this state, the value of $E_{ADJ}$ is more positive than the native coupon potential $E_N$ or the depolarized potential $E_{DEP}$ in the event that they differ. In the event that the current, $I_{ON}$, value (preferably statistically adjusted in the manner described above with respect to the $E_{OFF}$ data point measurements) is found to be positive, that is in a direction which is the reverse of the direction for applying protection to the buried metal object, the detection of that condition desirably also institutes priority state P1 so that, in either event, the pipe at the location at which the data points were measured would be designated as having no protection and is likely to be a current discharge point. In this priority state P1, the location of the test station for which the data is analyzed is designated as having the status of priority state one.

FIG. 4 illustrates priority state P2 in which the buried metal object is determined to be minimally protected and thus designated "fail". Priority state P2 is assigned to the test station when the value of $E_{ADJ}$ is more negative than $E_{DEP}$ by a voltage between 0 and 50 millivolts.

FIG. 5 illustrates priority state P3 in which the buried object is determined to be insufficiently protected at the region of the test station and is therefore designated as "fail". For priority state P3, the value of potential $E_{ADJ}$ is more negative than $E_{DEP}$ by an amount within the range of 50 to 100 millivolts.

FIG. 6 illustrates priority state P4 in which the buried object in the region of the test station is determined to be adequately protected and therefore is designated "pass". For priority state P4, the value of the potential $E_{ADJ}$ is more negative than that location's $E_{DEP}$ by a voltage in the range of 100 to 350 millivolts.

FIG. 7 illustrates priority state P5 in which the buried object in the region of the test station is determined to be over protected and therefore is designated "exceed". For priority state P5, the value of the potential $E_{ADJ}$ is more negative than $E_{DEP}$ by more than 350 millivolts.

The first four columns of FIG. 11 summarize these criteria.

Although the principles of the present invention are intended primarily for use with impressed current cathodic protection systems, the monitoring features of the invention may also be applied to sacrificial anode systems. However, it is believed impractical to control most sacrificial anode systems because their protection current can not be readily varied, although it is theoretically possible to provide a controllable, variable resistance in their circuit or switch additional, parallel connected sacrificial anodes into and out of connection in the protection circuitry and thereby control their protection current.

Rectifier Control

The assignment of priority states to the measurements taken for each coupon test station permits these priority states to be used to control the cathodic protection systems spaced along the buried object. More specifically, any desired change and the value of each desired change is determined by the central control-processing unit 30 and communicated through the data communication telemetry to each rectifier. A desired change is preferably calculated according to criteria in the algorithm of the invention. The change will be to an electrical parameter of each cathodic protection system or rectifier such as a desired change in its voltage or current output. For example, the voltage input to a voltage controlled rectifier is varied to change the voltage or current output of that rectifier.

For example, a response to priority state P1 causes an immediate increase in the level of protection of the rectifiers in the locality of the test station. Preferably these are adjusted upwardly by twenty percent relative to their previous level of protection. For example, for a linearly responsive voltage controlled rectifier, the control voltage input is increased by twenty percent if the test station detecting priority state P1 is designated as local to the rectifier. In the event that the test station is designated central, that is between two rectifiers, the protection level of both rectifiers may be increased by an equal amount, such as ten percent, so that the additional protection is distributed between the two rectifiers. This is done for each test station which exhibits priority state P1.

For each coupon test station for which priority state P2 is detected, a level of protection is increased by ten percent if the test station is associated with a "local" rectifier and if the test station is designated as central the ten percent is distributed between the rectifiers to which it is central so that each would be increased by five percent in the preferred embodiment.

In the event a coupon test station is detected to exhibit priority state P3, a local rectifier is increased by five percent, or if the test station is central, two nearby rectifiers are each increased by 2.5 percent.

In the event a coupon test station exhibits priority state P4, for which the protection is considered adequate, no adjustments are made to the rectifiers near that test station.

In the event a coupon test station exhibits priority state P5, so that it is over protected, if the test station is designated as local to a rectifier, the protection level of that rectifier is decreased by five percent. If that test station is designated central, the protection level of the two nearby rectifiers are decreased each by 2.5 percent.

The distributed rectifier adjustments described above may be distributed, preferably equally, over more than two rectifiers. Also, for all cases where an adjustment is made, other percentage changes may be adopted or, alternatively, quantitative changes, such as so many volts or amps, may be made.

Figure 10:
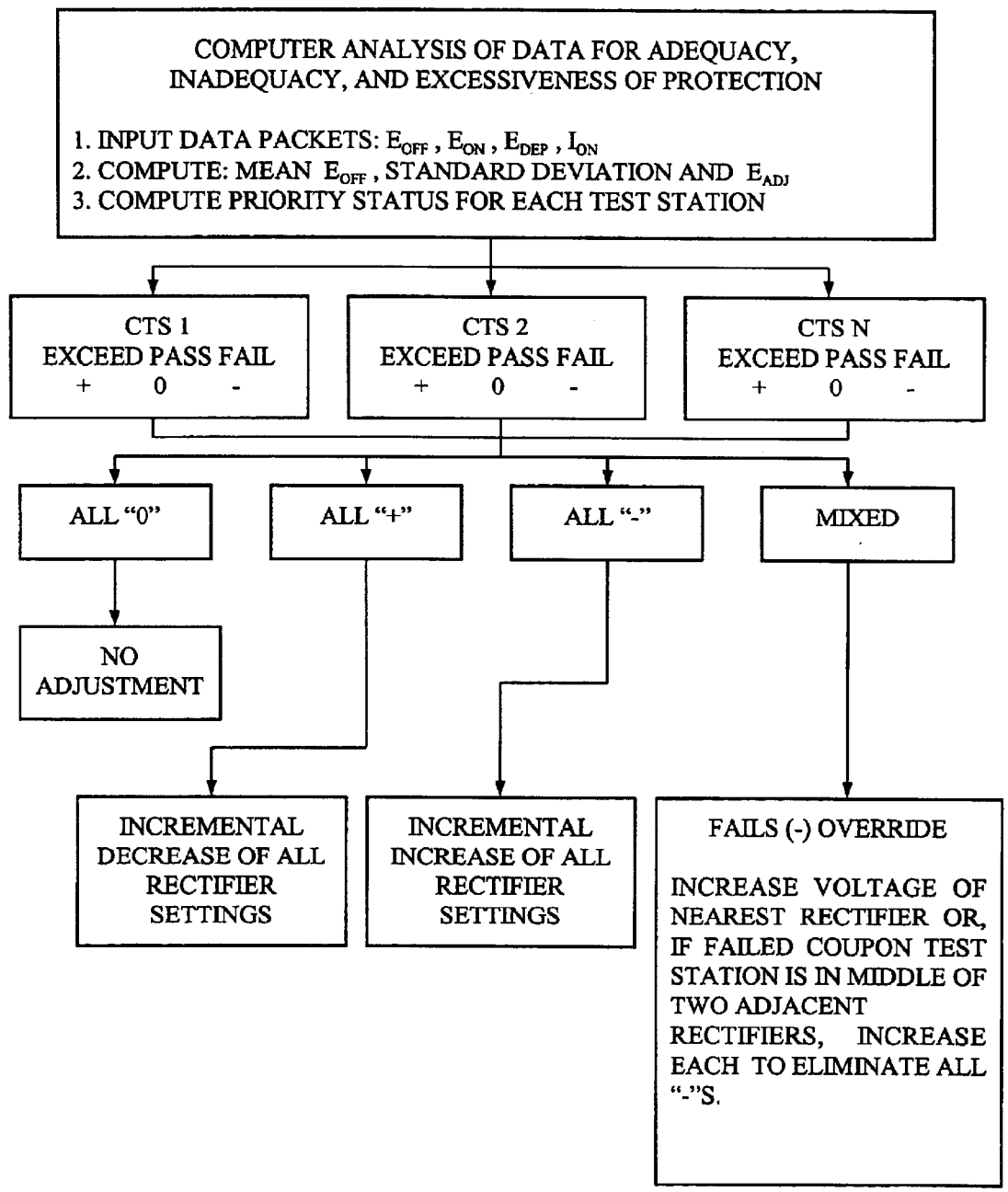
FIG. 10 is a flow chart illustrating a portion of the analysis method and algorithm which is preferred for use with the present invention.

FIG. 10 illustrates this operation for the system as a whole. As described above and illustrated in FIG. 11, the five priority states can be categorized (second column) as one of the three categories: fail, pass and exceed. As illustrated in the flow chart of FIG. 10, one of these three categories is detected and assigned for each coupon test station. The computer then applies the rectifier setting adjustment algorithm described above for each cathodic protection rectifier. In the event all test stations provide measurements which fall in the pass category, no adjustments are made to the rectifiers. In the event all test stations are categorized as "exceed", which is priority state P5, then all rectifier settings are incrementally decreased in the manner described above or in some alternative manner. In the event all test stations fall into the category of "fail", then all rectifiers are incrementally increased in amounts determined by the priority states of their nearby coupon test stations in the manner described above or an alternative manner. Finally, if the test stations fall into different categories, then each rectifier is adjusted in accordance with the priority state in which its nearby coupon test stations fall, as a result of their measurements, in the manner described above or a suitable alternative. In the event one test station associated with a rectifier falls into a "pass" category and another test station associated with the same rectifier falls into the "fail" category, the "fail" category overrides the "pass" category and corrective action is taken.

Persons skilled in the art will recognize that the designations used herein, such as "exceed", "pass", "fail", "local", "central", "no protection", "minimally protected", "insufficiently protected", "adequately protected", and "overly protected" or "excessively protected" as well as the algebraic representations of potentials using the letter "E" with subscripts, are all arbitrary designations to the extent they are literal labels for the technical conditions which they represent. The literal labels themselves are not necessary to the invention and suitable alternative labels for the same technical conditions may be used. In computer memory there may be other, separate and unique alphanumeric data words selected to represent the same kinds of technical conditions. Consequently, the labels referred to in the specification and claims represent any unique data words selected to designate the technical conditions which those labels represent.

Urgency Criteria

Although the rectifer control responses to the priority states may be effected immediately upon detection, for some states it is preferable to require multiple detections of the state before initiating the control response. The different priority states can be assigned attributes of differing urgency levels by the computer program based upon the nature of the detected state. This is preferable, though not necessary, with the present invention.

Since priority state P1 results from the detection of an absence of protection, it has the highest urgency and the response to its detection is preferably applied immediately. Upon detection of priority state P1 as a result of data derived from a coupon test station, the rectifiers for which the coupon test station has the attribute of "local" and "central" are adjusted as described above.

Priority states P2, minimally protected, and P3, insufficiently protected, ordinarily do not require an immediate control response. For these, the central control-processing unit maintains a count of the number of occurences of each state for each coupon test station. After a selected number of recurrences of the states are detected, the control response is implemented and all the counters are reset to zero. For example, taking into account the greater urgency for the detection minimal protection than for inadequate protection, the system waits for two occurrences of priority state P2 or three occurrences of priority state P3. When the count of either accumulates the assigned number of counts as a result of data derived from a coupon test station, the rectifiers for which the coupon test station has the attribute of "local" and "central" are adjusted as described above. It is apparent that different count criteria can be used.

Consequently, the urgency level attribute bears an inverse relationship to the number of counts which must be accumulated before a control response is implemented. Each time a coupon test station is polled, a counter for each of priority states P2, P3 and P5 for each test station is incremented. The higher the urgency of the priority state, the fewer counts which are accumulated before remedial action is taken.

Because priority state P4 represents adequate protection and therefore no control response is appropriate, no counts need be accumulated.

Priority state P5, overprotection, requires a control response when that state has been detected several times, for example three times.

The use of urgency criteria avoids unnecessary oscillation of the cathodic protection applied to the buried object, such as can occur when the detected values are near the boundaries of the contiguous intervals of potentials used to define the priority states and noise or other minor signal variations cause temporary erroneous data.

While certain preferred embodiments of the present invention have been disclosed in detail, it is to be understood that various modifications may be adopted without departing from the spirit of the invention or scope of the following claims.

APPENDIX

**COUPON MONITORING FOR CATHODIC PROTECTION OPTIMIZATION:
REAL-TIME AUTOMATED REMOTE CONTROL
OF DYNAMIC STRAY CURRENT ON PIPE-TYPE CABLES**

M. Yunovich and N. G. Thompson
C C Technologies
6141 Avery Road
Dublin, OH 43016-8761

ABSTRACT

Stray-currents represent a significant problem for integrity of pipe-type cables. Pipe-type cables (feeders) are generally outfitted with impressed current cathodic protection (CP) systems and have an external coating. Unfortunately, the coatings are imperfect in that there are holidays and disbonded sites, and the effectiveness of CP system in the presence of stray current is difficult to measure. An approach to assess the effectiveness of cathodic protection in dynamic stray current conditions, consisting of monitoring the IR-drop free polarization ($E_{off}$) potentials of multiple Coupon Test Stations (CTSs), buried in close proximity to the monitored feeder has proven to be successful. The CTSs act as a backbone for the CMCPO system, which performs a real-time analysis of the instant $E_{off}$ potentials, and zero-resistance ammeter currents downloaded from the individual CTSs, categorizes the existing corrosion conditions along the monitored structure according to a customizable algorithm, and uploads the solutions to the remotely controlled CP rectifiers. This system provides the ability to remotely monitor and control CP of pipelines in stray current areas more accurately than ever before. The paper offers quantitative assessment of the CMCPO system performance and benefits.

INTRODUCTION

Pipe-type cables (also known as feeders) have been used for electric power transmission since the 1930's.[1,2] The largest number of cables of this type has been installed since the 1950's. These buried cable systems consist of the phase conductors, insulating material, a dielectric fluid for cooling and insulation, and an outer steel pipe. The pipe jacket is often coated with a dielectric coating for corrosion mitigation, and the cable is generally installed in a thermal insulating backfill (such as sand).

Despite the fact that the pipe-type cables are coated, industry experience with buried pipelines of all types has shown that coatings are not perfect.[3] The primary purpose of the coating is to provide a dielectric barrier between the steel substrate and the soil environment, which can sustain the corrosion process of the steel pipe. Flaws or pinholes in the coating, known as holidays, allow the metal substrate to be directly exposed to the soil electrolyte, thereby causing corrosion at that location.

Pipe-type cables are generally afforded corrosion control by cathodic protection (CP) in addition to protective coatings. The effectiveness of the cathodic protection systems in controlling corrosion of steel piping is predicated on proper operation and maintenance of the CP system, as well as monitoring to ensure that the minimum criterion for corrosion control is being met. However, despite installed CP systems, the pipe-type cables are reported to have experienced corrosion-related leaks. Feeder cables in complex utility environments can be subjected to stray currents as the result of the application of cathodic protection to foreign pipelines and stray currents emanating from sources such as DC transit systems. Stray current corrosion is a major contributor to the corrosion being experienced on the pipe-type cables.

NATURE OF THE PROBLEM

The DC stray currents contribute to corrosion of the pipe-type cables (and any steel underground structure for that matter) in two ways: (1) causing rapid metal loss at the pipe locations serving as the current discharge points and (2) introducing an additional IR-drop error in grade-level potential measurements. In order for the measurements to be reliable, no current flow should be present in the path between the buried pipe-type cable and the reference electrode. While de-energizing of the impressed current CP system synchronously with the potential measurements is relatively easy, simultaneous elimination of the stray currents, particularly in the urban environment, is a virtual impossibility. Hence, the off-potential values obtained at grade level may still contain significant IR-drop components, which precludes an accurate estimation of the feeder CP efficiency.

One approach to minimize the IR-drop in presence of DC stray currents is to use Coupon Test Stations buried in close proximity to the monitored structure. A number of CTS design exists; one such design, developed by CC Technologies Laboratories, Inc. in association with PRCI, consists of two steel elements (with an area of 1.4 in$^2$) with a plastic tube (see Figure 1), positioned within 0.5 in. of the top of the steel elements (coupons).

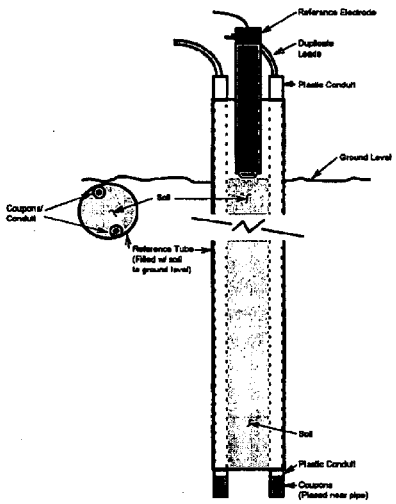

FIGURE 1 – Coupon Test Station schematic.

One of the elements ("Polarized" or "CP Coupon") is electrically connected to the buried structure. When the CP Coupon is connected to the pipe, it simulates a similarly sized defect in the pipe coating and is, therefore, subject to the same stray current influences. Upon interruption of the CP Coupon-pipe connection, not only is the CP current is interrupted, but the stray current is interrupted also. In other words, upon interruption, the CP Coupon becomes a point defect, free from the DC current effects.

During an interrupted, off-potential measurement, the Polarized Coupon is briefly disconnected from the structure, yielding an IR-drop-free potential ($E_{off}$) of the Coupon. The CTS configuration also allows for measuring the current passing between the CP Coupon and the protected structure. An example of the on- and off-potential measurements obtained from a CTS installed next to an actual pipe-type cable located in a major metropolitan area is shown in Figure 2; the figure also shows the zero-resistance ammeter current between the feeder and the CP Coupon.

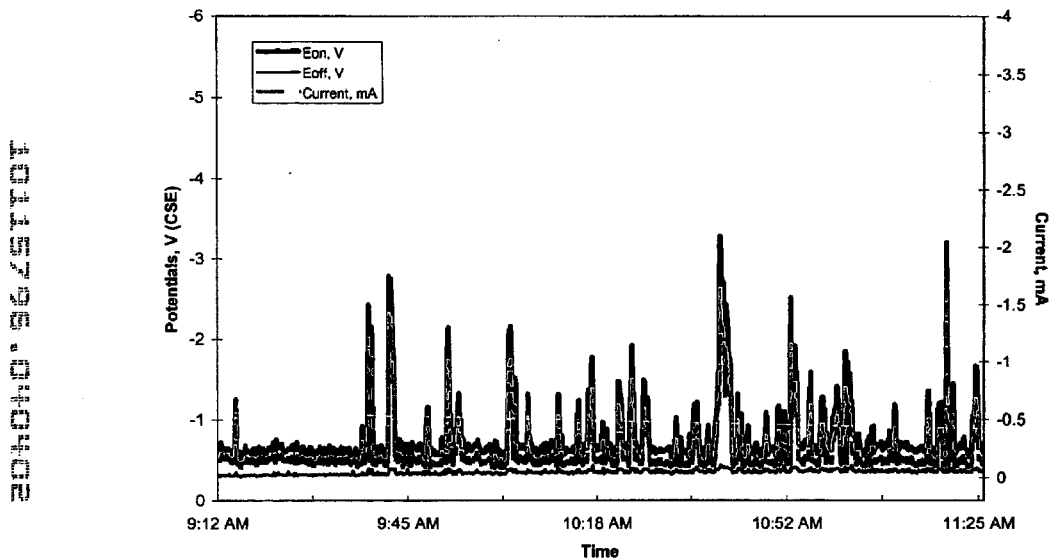

FIGURE 2 – On- and off-potential measurements from a CTS in a stray current environment.

The magnitude of the IR-drop caused by the stray current, as manifested by the difference between the on-potential and off-potential ($E_{on}$ and $E_{off}$) curves, is quite high, at times exceeding -2.8V. Another important observation gleaned from the graph is that despite the current being picked up by the Polarized Coupon (negative sign), the off-potential values are significantly below the NACE CP protection criterion of –850mV (CSE).

Furthermore, the graph in Figure 2 points to yet another problem posed by the DC stray currents – their dynamic nature. In a course of 3 hours during which the data was collected, the $E_{on}$ values ranged from –0.49 to –3.24V (CSE) with the corresponding current fluctuating from –0.08 to –1.61mA. Although in the illustrated example the current remained negative (cathodic), there exists a certain probability that other coating holidays on the protected structure may serve as current discharge sites.

Hence, considering the magnitude of the stray currents and their dynamic nature, affected structures may require more than just once-a-year adjustments to the impressed current CP output. The periodicity of these adjustments would depend on the temporal dependence of the stray current activity, i.e., in the areas where the DC stray currents originate from, e.g., an electric transit system, such activity is likely to be associated with the peak hours and thus be more predictable. Even though, the changes to the rectifier output would be necessary several times a day. If there are multiple sources of the DC stray currents, the situation becomes more complicated. In addition, seasonal changes in soil conditions (such as moisture content) can alter CP current requirements and rectifier(s)' output.

As pipe-type cables transmit electricity from power plants to substations, they are commonly located in urban environments with a variety of DC stray current sources. The presence of cooling oil filling in the interstitial space between the outer jacket and the inner steel pipe turns corrosion-related failures into costly environmental clean-up projects, often exacerbated by the need to restore excavated pavements as soon as possible and the need for traffic control.

APPROACH

In order to address the issue of cathodic protection of pipe-type cables in dynamic DC stray current conditions, a system was required that could detect the shifts in on- and off-potentials of the pipe and automatically adjust CP levels. In other words, such system would constantly optimize CP current to ensure that the off-potentials are within protective range.

Due to the IR-drop introduced by the DC and transient stray currents, such system should be capable of acquiring error-free off-potentials of the pipe-type cable (via the use of e.g., Coupon Test Stations).[1] Other critical pertinent issues are (1) the choice of protection criterion and (2) the choice of reference electrode.

Protection Criterion

The criterion selected for the CMCPO control system is 100 mV of polarization (depolarization) of the Polarized Coupon. The polarization criterion is defined as the difference between the Polarized Coupon and the reference electrode (freely corroding Coupon of the CTS assembly) – see discussion below.

Reference Electrode

Continuous monitoring for controlling the CP system requires a permanent reference electrode. It was decided to utilize the second coupon of the CTS assembly ("Native Coupon") as the reference electrode. There are several benefits to utilizing the Native Coupon as a reference electrode.

- The Native Coupon represents the free-corrosion conditions for steel in the soil environment near the pipe-type cable surface.

- A 100 mV polarization criterion can be applied by measuring the off-potential of the Polarized (CP) Coupon versus the free-corrosion potential of the Native Coupon.

- Concerns over the differences in the Native Coupon open-circuit potential and the *depolarized* potential of the CP coupon can be addressed by periodically measuring this difference and adding it to the 100 mV criterion for establishing the target CP control potential.

This design of the CMCPO system allows for a continuous adjustment of the absolute potential value of the CP criterion (i.e., the target control potential value)

---

[1] The system described below is referred to as Coupon Monitoring for Cathodic Protection Optimization (CMCPO). Patent pending.

to account for changes in soil conditions due to the seasonal changes (e.g., moisture content) and fluctuations in the level of the stray current activity. In the past, one serious concern was whether a target control potential based on the 100 mV criterion (determined once a year) ensured sufficient protection during all year. By referencing the 100 mV polarization to a Native Coupon that goes through the same varying moisture conditions as the CP Coupon, continuous updating of the criterion can be accomplished.

It is mentioned earlier that another major concern was whether the Native Coupon open-circuit potential remains to be the appropriate reference for the application of the 100 mV depolarization criterion[1]. To address the issue, the difference between the Reference Coupon potential and the long-term, depolarized CP Coupon potential is periodically measured (once or twice a year). Adjustments to the 100 mV criterion are done by adding this measured potential difference to the 100 mV. Yet, another concern pertains to the stability of the Native (Reference) Coupon open-circuit potential. It is believed that the stability of this potential is adequate, and that the only significant fluctuations are due to changes in the soil environment around the Native Coupon. The stability issue was examined further during the field testing phase.

Basic Concept

The basic principle for the control methodology is that the changes in the corrosion conditions of the pipe-type cable due to stray current transients are manifested by changes in on-potential, off-potential, and current ($E_{on}$, $E_{off}$, and $I_{ZRA}$) of a Polarized Coupon of a CTS assembly buried near to, and connected to, the pipe-type cable. These values are obtained from the Polarized (CP) Coupon of a CTS assembly. The CMCPO system general configuration is depicted in Figure 3. The example used to illustrate the concept includes three CTS units for

---

[2] The depolarization criterion by virtue of its measurement via depolarization accounts for long-term (permanent) difference between the fully depolarized potential and the original free-corrosion potential. These differences are attributed to the formation of cathodic reaction products during CP, which can result in changes in the environment in contact with the protected steel surface or changes in films formed directly on the steel surface.

monitoring corrosion conditions and two rectifiers on either end of a section of pipe-type-cable. The Coupon Test Stations are installed at critical locations. Which locations are critical is determined by analyzing CP survey data, repair records and other germane information (such as stray current activity, soil resistivity, etc.). Identifying maximum stray current discharge locations along pipe-type cables is particularly important.

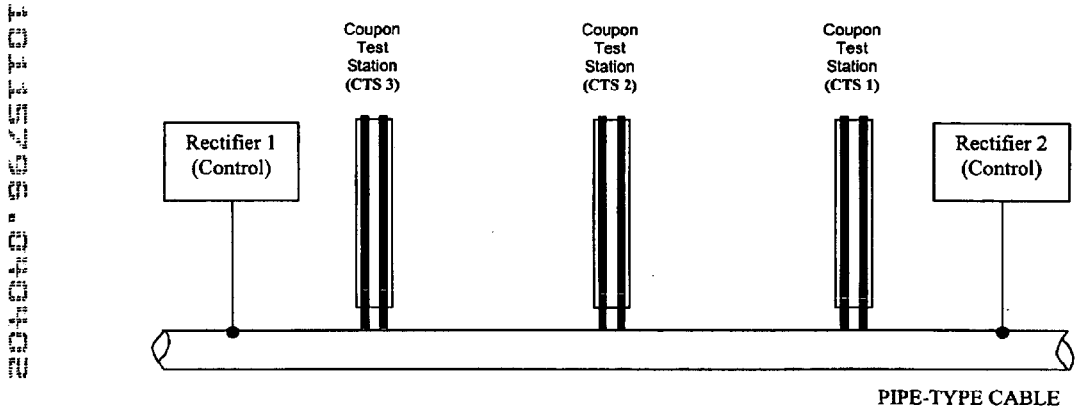

FIGURE 3 – Schematic of a simplified CP system for a pipe-type cable with CTS monitoring.

Each CTS location requires a data acquisition unit with remote access and data transmission capabilities. The Coupon potential and current data are gathered using a Coupon monitoring instrument (CM3400)[2]. The rectifiers employed by the CMCPO system require digital remote control capabilities, and a data acquisition/transmission unit similar to that in use at the CTS location.

---

[3] Model CM 3400 Coupon Monitor by CC Technologies Systems, Inc.

The potentials of the Polarized Coupon are measured in reference to the Native Coupon. The measured potentials are continuously collected and uploaded by a data acquisition unit via appropriate means of communication (land line or cellular phone) to a central computer, which polls the CTS locations at preset time intervals (e.g., once an hour). The computer completes statistical processing of a data packet from a single CTS and compares the processed $E_{off}$ potentials to the chosen protection criterion (100 mV of polarization). Upon comparison, the corrosion condition at the CTS location is classified as one of the so-called Priority States, depending on the extent the average $E_{off}$ value deviates from the protection criterion.

The processed values and the Priority State are stored. At that point, the central unit polls the next CTS, and process is repeated until the data packets from all the installed CTS have been received and Priority States determined.

The computer then follows a specially developed software-based algorithm, which takes into the account not only the severity of corrosion condition at each CTS (i.e., the Priority State), but also the CTS position along the feeder and the sequence of Priority States at each CTS. If needed, the computer then generates a solution (i.e., whether the rectifier settings should be adjusted) and sends the command to the rectifier(s). The system shown in Figure 3 has two rectifiers and any given solution may require adjustments to one or both. A simplified example of the algorithm is shown in Figure 4.

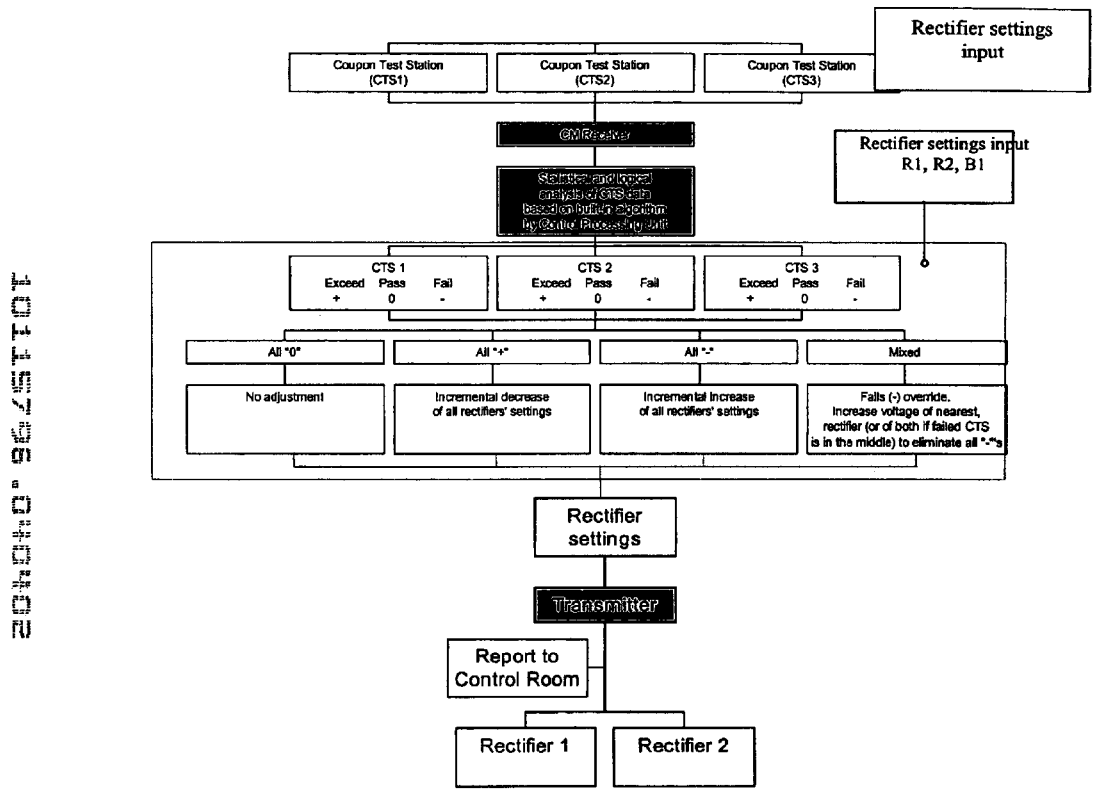

FIGURE 4 – Simplified logic algorithm for analyzing CTS data.

As mentioned above, the processing of the data packet downloaded from a CTS results in the following prioritized responses:

- Three categories for underprotection (P1, P2, and P3) designated as "Fail" in Figure 4.
- One category for overprotection (P5) designated as "Exceed" in Figure 4.
  One category for adequate protection (P4) designated as "Pass" in Figure 4.

The algorithm treats different Priority States differently, i.e., Priority P1 (defined as 'No protection') requires an immediate response, whereas Priorities P2 and P3 (defined as 'Minimal protection' and 'Insufficient protection', respectively) are attended to only after a certain number of these Priorities take place at any given CTS. Furthermore, the extent to which the rectifier output is adjusted varies depending on the Priority State, with P1 receiving the maximum (in percent of the output) preset change upward. Priority P5 (defined as 'Overprotection') requires attention when significant cathodic polarization of the CP coupon has been registered for several polling cycles. To avoid damage to the coating due to excessively negative protection potentials, the CP current is decreased. The CMCPO system can also downgrade the rectifier output if the adverse stray current conditions change with time.

There is only a minimal (several minute) delay between when distress conditions are discovered at one or several locations at the feeder and the moment the rectifier(s) get the appropriate command. The delay time is user-selectable, but the minimal delay time is defined by the time required for the data download, i.e., the baud rate of the data transmission.

Field testing

A working prototype of the CMCPO was installed on a pipe-type cable located in a major metropolitan area in the United States. The feeder, about 5 miles long, was outfitted with three Coupon Test Stations and had two remotely controlled rectifiers (70V, 30A output capacity). The choice of the CTS locations was predicated partially on the existing CP survey results over several years and partially on the accessibility of the sites. In late 1997, the stations were installed next to the feeder (in a bulb of sand backfill) inside the existing test boxes, flush with the surface. The installation procedure of a CTS is illustrated in Figure 5. The instrumentation boxes housing the data acquisition units were installed in the manholes adjacent to the test boxes.

The system was tested on a continuous basis for more than a year and a half. In order to achieve stable open-circuit potential readings from the Reference Coupons of the CTS assemblies, the CMCPO was energized approximately one year after the CTS were installed; during the period of inactivity, the CP Coupons were electrically connected to the feeder to prevent corrosion.

The issue of the stability of the open-circuit potentials of the Reference Coupons of the CTS assemblies was critical for the successful operation of the CMCPO and these potentials were periodically measured against Copper/Copper Sulfate standard reference electrode. The summary of the measurements is presented in Table 1.

FIGURE 5 – Installation of a Coupon Test Station inside a test box.

TABLE 1 – Summary of the Reference (Native) Coupon open-circuit potentials.

| Station Location | | Native, V (vs. CSE) 11/97 | Native, V (vs. CSE) 10/98 |
|---|---|---|---|
| CTS 1 | Maximum | -0.452 | -0.448 |
| | Minimum | -0.556 | -0.456 |
| | Mean | -0.529 | -0.450 |
| CTS 2 | Maximum | -0.708 | -0.732 |
| | Minimum | -0.732 | -0.740 |
| | Mean | -0.723 | -0.736 |
| CTS 3 | Max | -0.368 | -0.476 |
| | Min | -0.424 | -0.504 |
| | Mean | -0.401 | -0.497 |

As seen, there are variations in the values obtained in 1997 and in 1998. The variability was expected, as the Native Coupon potentials are sensitive to such environmental conditions as, e.g., moisture levels in the ground, oxygen availability, etc., which tend to change with the seasons. In addition, the 1997 data was collected after some work was done to the station installations, and the assemblies had to be disturbed. These observations are consistent with the treatment of the use of the Native Coupons as reference electrodes, which require occasional infrequent adjustments to the target potential values for additional optimization of the system's performance.

Figures 6-8 show the Priority States at the three CTSs over the first six months of the field testing. [The vertical lines on the graphs indicate the date when one of the CMCPO system control rectifiers sustained a failure and was physically replaced with the second control rectifier, brought over from its location at the pipe-type cable.] Histogram analysis of the Priority States for each of the CTS location yielded the results summarized in Table 2.

The results are consistent with the relative position of the CTSs and CP system configuration. The major conclusion is that at monitored locations, the level of protection is adequate for more than 80% of the time and, for CTS 1 and 3, more than adequate.

Coupon Test Station 3 was placed in the vicinity of Rectifier 1 and is overprotected about 87% of the time, and adequately protected about 12% of the time. Shutting down Rectifier 1 caused an immediate shift in the Priority states from P5 to P4 and, on a number of occasions, to P1.

Rectifier 2 had a high resistance groundbed and supplied very limited current; while being close to Rectifier 2, CTS 1 has nonetheless been overprotected for more than 97% of the time (the reason for this is not known). It is therefore understandable that there was no effect on the protection level once Rectifier 2 was shut down permanently.

Monitoring of the CTS 2 and CTS 3 locations (Figures 7 and 8) shows that the protection was at or above an adequate level for more than 88% and 99% of the time, respectively.[3] Shutting down of Rectifier 1 had only a marginal effect on CTS 2, causing a short string of Priority 1 (no protection) conditions shortly after the shutdown. There was a notable increase in the number of P4 states (adequate protection) at the CTS 3 site.

A better illustration of the system's operation can be obtained by examining Figure 9, which combines the Priority State data with the output voltage at CTS 3, collected after the system has been in operation for one year.

The only remaining controlled rectifier on the system suffered another failure in late October 1999; it was put back in service late November 1999. For the one-month period, the

---

[3] The pipe-type cable had another rectifier, which was not a part of the CMCPO system, located in the vicinity of CTS 3 and affected CTS 3 and CTS 2 locations.

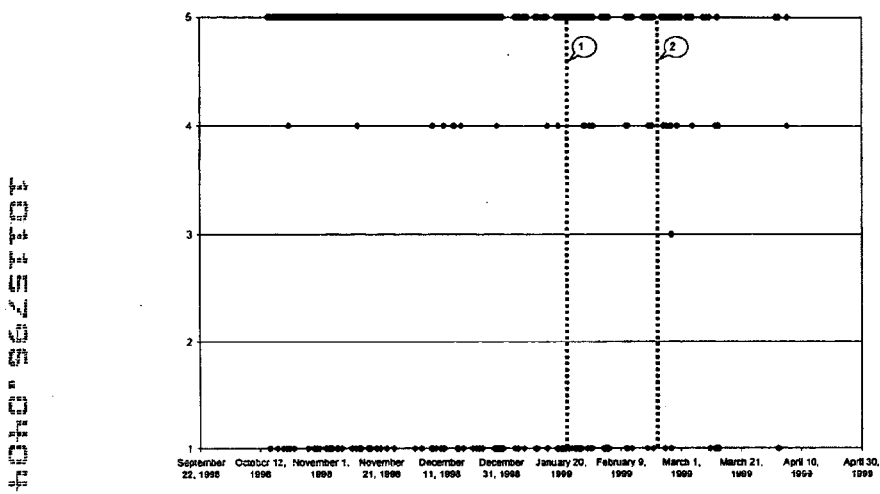
FIGURE 6 – Priority States at CTS 1. Line 1 denotes Rectifier 1 shutdown; Line 2 denotes replacement of Rectifier 1 with Rectifier 2.[4]
---
[4] In October 1998, one of the rectifiers suffered a failure and was replaced with the remaining CMCPO rectifier.

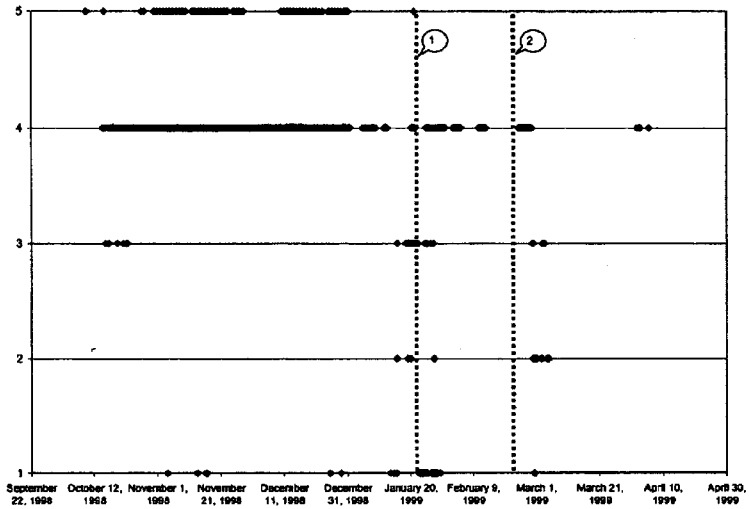
FIGURE 7 – Priority States at CTS 2. Line 1 denotes Rectifier 1 shutdown; Line 2 denotes replacement of Rectifier 1 with Rectifier 2.
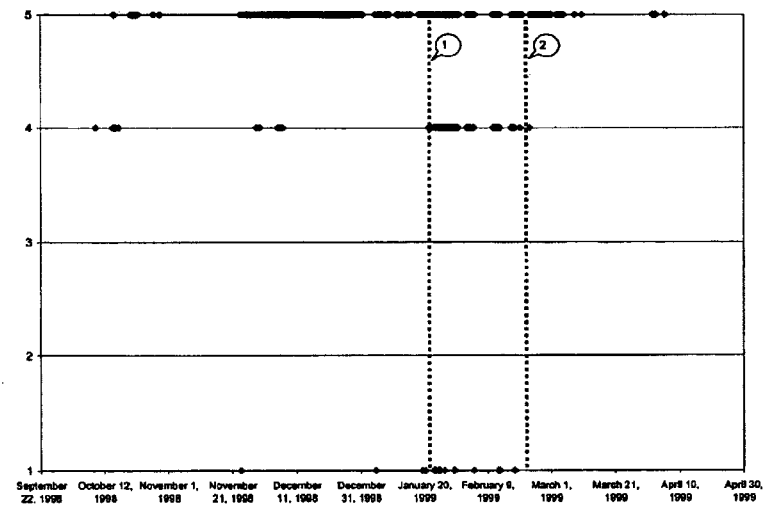
FIGURE 8 – Priority states at CTS 3. Line 1 denotes Rectifier 1 shutdown; Line 2 denotes replacement of Rectifier 1 with Rectifier 2.

TABLE 2 – Histogram analysis of Priority States for each CTS location.

| Priority | Percent at Priority State | | |
|---|---|---|---|
| | CTS 1 | CTS 2 | CTS 3 |
| 1 | 1.96 | 3.95 | 0.51 |
| 2 | 0.00 | 2.99 | 0.00 |
| 3 | 0.04 | 4.67 | 0.00 |
| 4 | 0.57 | 82.84 | 12.15 |
| 5 | 97.43 | 5.55 | 87.34 | system effectively operated in a monitoring mode. This yielded an opportunity to successfully demonstrate the high sensitivity of the monitoring based on the CTS technology. As an example, the table below (Table 3) shows the results of a histogram analysis of Priority States at CTS 3 (near Rectifier 1) with one controlled rectifier running and with no controlled rectifiers.[5]

---

[5] The non-CMCPO rectifier remained operational, which accounts for the fact that the CTS 3 Priority States did not drop below P4.

What is claimed is:

1. An improved coupon test station for measuring the adequacy of cathodic protection for mitigating the corrosion of a metal object buried in soil, the test station having a first coupon of substantially the same metal as the buried object to form an electrode for contact in the soil and for connection to the buried metal object and a second coupon of substantially the same metal as the buried object to form an electrode for contact in the soil, wherein the improvement comprises:

a voltage detector circuit connected to both coupons for measuring the potential of the first coupon, while the first coupon is disconnected from the buried object, with reference to the second coupon, which is not electrically connected to cathodic protection so it is freely corroding.

2. A test station according to claim 1 wherein the voltage detector circuit is connected to a data storage for storing the value of the detected potential.

3. An automated data collection and control system for a cathodic protection system for inhibiting corrosion of a metal object buried in soil, the object being associated with a multiplicity of cathodic protection circuits electrically connected to and at spaced intervals along the object, the apparatus comprising:

(a) a multiplicity of test stations at spaced intervals along the object, each test station including
   (i) at least one buried reference electrode;
   (ii) a polarized coupon switchable into electrical connection with the object and having a metallurgical composition similar to the object; and
   (iii) an electrical parameter detection circuit in electrical connection to at least the polarized coupon;
(b) a coupon monitoring, data storage and data communication circuit connected to the detection circuit for storing and transmitting detected values of the parameter;
(c) a data communication telemetering system connected to the coupon monitoring, data storage and data communication circuit for transmitting data representing electrical parameter values detected by the detection circuit to a central location; and
(d) a remotely located central control-processing unit connected to the data communication telemetering system for acquiring and storing data from each test station representing the values detected at each test station for subsequent data processing and display, the central control-processing unit also being controllably connected to the cathodic protection circuits, the central control-processing unit having stored data and instructions for analyzing the data and determining the adequacy, inadequacy and excessiveness of the cathodic protection of the buried object in the vicinity of each test station and having stored data and instructions for controllably adjusting an electrical, cathodic protection parameter of each of the cathodic protection circuits in response to inadequate or excess protection.

4. An apparatus in accordance with claim 3, wherein the reference electrode of each test station is a buried native coupon, the native coupon having a metallurgical composition substantially the same as the object.

5. An apparatus in accordance with claim 3 wherein the detection circuit is a voltage detection circuit, the detection circuit is also connected to the reference coupon and the electrical parameter is the voltage between the reference electrode end the polarized coupon.

6. An apparatus in accordance with claim 5, wherein the reference electrode of each test station is a buried native coupon, the native coupon having a metallurgical composition substantially the same an the object.

7. An apparatus in accordance with claim 3 wherein the detection circuit is a current detection circuit and the electrical parameter is the electrical current flowing through the electrical connection between the polarized coupon and the buried object.

8. A method for monitoring a multiplicity of cathodic protection circuits electrically connected to a buried metal object and including a multiplicity of buried anodes at spaced locations along, and spaced from, the object, the method comprising:

(a) burying a polarized coupon having a metallurgy similar to the metal object at each of a multiplicity of test stations spaced along the object, the polarized coupon being normally connected to the buried object;
(b) at each test station detecting an electrical parameter associated with the polarized coupon at the location;
(c) telemetrically communicating data representing the detected parameter from each test station to a remotely located central control-processing unit computer; and
(d) storing at the central computer the communicated data from each test station representing the values detected at each test station, in accordance with stored instruction, for subsequent data processing and display;
(e) analyzing the communicated data at the central computer, in accordance with stored-Instructions and data, for the adequacy, inadequacy and excessiveness of the cathodic protection of the buried object in the vicinity of each test station and storing data representing the results of die analysis;
(f) analyzing the data representing said results at the central computer, in accordance with stored instructions and data, for determining a desired change in an electrical parameter of each cathodic protection system; and then
(g) communicating data to cathodic protection systems in the vicinity of test stations at which the cathodic protection was found inadequate or excessive for controllably adjusting the electrical parameter.

9. A method in accordance with claim 8 wherein the detected parameter is electrical current between the polarized coupon and the buried object.

10. A method in accordance with claim 8 wherein the method further comprises burying a reference electrode at each test station and the detected parameter is the voltage between the reference electrode and the polarized coupon and is detected while the polarized coupon is connected to the buried object.

11. A method in accordance with claim 8 wherein the method further comprises burying a reference electrode at each test station, electrically disconnecting the polarized coupon from the buried object, waiting for a selected time interval to permit the polarized coupon to depolarize and wherein the detected parameter is the voltage between the polarized coupon and the reference electrode and is detected after the time interval.

12. A method in accordance with claim 8 wherein the method further comprises burying a reference electrode at each test station, electrically disconnecting the polarized coupon from the buried object, and wherein the detected parameter is the voltage between the polarized coupon and the reference electrode measured before the polarized coupon becomes depolarized.

13. A method in accordance with claim 8 wherein the stored instructions and data for determining a desired change in an electrical parameter of each cathodic protection system includes determining the change in a cathodic protection system as a function of the electrical parameters measured at multiple test stations.

14. A method in accordance with claim 13 wherein the electrical parameters are detected and communicated multiple times daily.

15. A method in accordance with claim 13 wherein the polarized coupon is disconnected from the buried object and permitted to depolarize for a selected time interval and wherein the potential of the, polarized coupon is measured while in its depolarized state and stored in the central computer.

16. A method in accordance with claim 15 wherein the potential, $E_{DEP}$, of the polarized coupon while in its depolarize state is measured with reference to the native coupon.

17. A method in accordance with claim 13 wherein the burying step includes burying a reference electrode which is a native coupon having a metallurgy substantially the same as the metallurgy of the buried object.

18. A method in accordance with claim 13 wherein further comprising electrically disconnecting the polarized coupon from the buried object, wherein the detected parameter is the voltage, $E_{OFF}$, between the polarized coupon and the reference electrode measured after the polarized coupon is disconnected from the buried object and before the polarized coupon becomes depolarized, and wherein the step of analyzing the communicated data further comprises subdividing possible $E_{OFF}$ potential measurement values into a plurality of contiguous voltage ranges and assigning a different state to each range, the ranges having the states of insufficient protection, adequate protection and overprotection.

19. A method in accordance with claim 18 and further comprising communicating data to the cathodic protection systems for controllably adjusting the electrical parameter by:

(a) increasing the cathodic protection by a preselected amount for at least one cathodic protection circuit in the vicinity of each test station at which cathodic protection was inadequate; and (b) decreasing the cathodic protection by a preselected amount for at least one cathodic protection circuit in the vicinity of each test station at which the cathodic protection was excessive.

20. A method in accordance with claim 18 wherein the ranges further include the states of no protection and minimally protected.

21. A method in accordance with claim 20 wherein (a) the telemetrically communicated data represents a plurality of detected potentials from each test station to form a set of potentials;

(b) the set of potentials is statistically analyzed to detect the sum, $E_{ADJ}$, of the mean and the standard deviation to provide a composite value of the polarized potential; and (c) the difference between $E_{ADJ}$ and $E_{DEP}$ is calculated and the range into which the difference falls is calculated to determine and assign to the difference the protection state for the range into which the difference falls.

22. A method in accordance with claim 21 and further comprising communicating data to the cathodic protection systems for controllably adjusting the electrical parameter by:

(a) increasing the cathodic protection by a first preselected amount for each cathodic protection circuit in the vicinity of each test station at which the cathodic protection had the status of no protection;

(b) increasing the cathodic protection by a second preselected amount for each cathodic protection circuit in the vicinity of each test station at which the cathodic protection bad the status of minimally, protected, the second amount being less than the first amount;

(c) increasing the cathodic protection by a third preselected amount for each cathodic protection circuit in the vicinity of each test station at which the cathodic protection had the status of insufficient protection, the third amount being less than the second amount;

(d) decreasing the cathodic protection by a preselected amount for each cathodic protection circuit in the vicinity of each test station at which the cathodic protection had the status of excessive; and (e) waking no change in the cathodic protection for each cathodic protection circuit in the vicinity of each test station at which the cathodic protection had the status of adequate protection.

23. A method in accordance with claim 22 wherein an attribute representing "local" is assigned to each coupon test station which is substantially nearer to one rectifier than any other and an attribute representing "central" is assigned to each coupon test station which is substantially central to two rectifiers, and wherein the preselected amount of the increasing and decreasing steps is applied wholly to rectifiers for which the test station has the attribute "local" and is distributed between neighboring rectifiers for which the test station has the attribute "central".

24. A method in accordance with claim 22 wherein the method further comprises implementing urgency criteria by accumulating a count of the number of recurrences of at least the status of inadequate protection and minimal protection and implementing the increasing steps in response to the accumulation of a selected number of recurrences of a status.

25. A method for detecting a potential which substantially represents the polarized potential of a metal object buried in soil and connected to a cathodic protection system, the method comprising:

(a) burying in the soil a first coupon of substantially the same metal as the buried object to form an electrode for contact in the soil and for connection to the buried metal object;

(b) burying a second reference coupon of substantially the same metal as the buried object to form an electrode for contact in the soil, the second coupon being maintained substantially not connected to the cathodic protection system so that it is essentially freely corroding in the soil;

(c) electrically connecting the first coupon to the buried metal object and permitting it to become polarized;

(d) disconnecting the first coupon from the buried metal object; and (e) measuring the potential of the first coupon with reference to the second coupon while the first coupon is disconnected from the buried metal object.

26. A method in accordance with claim 25 and further comprising storing the measured potential in a data storage.

* * * * *